(12) United States Patent
Sirkar et al.

(10) Patent No.: US 6,986,847 B2
(45) Date of Patent: Jan. 17, 2006

(54) METHOD AND APPARATUS FOR ISOLATION AND PURIFICATION OF BIOMOLECULES

(75) Inventors: Kamalesh K. Sirkar, Bridgewater, NJ (US); Robert G. Luo, Boyds, MD (US); Yanke Xu, Bound Brook, NJ (US); Xiao-Ping Dai, Flemington, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 10/436,353

(22) Filed: May 12, 2003

(65) Prior Publication Data
US 2004/0069710 A1 Apr. 15, 2004

Related U.S. Application Data

(60) Provisional application No. 60/379,477, filed on May 10, 2002.

(51) Int. Cl.
*B01D 61/18* (2006.01)
*B01D 15/08* (2006.01)

(52) U.S. Cl. ............... 210/650; 210/198.2; 210/321.6; 210/321.89; 210/506; 210/656; 427/245

(58) Field of Classification Search ............... 210/634, 210/638, 639, 645, 650, 656, 198.2, 321.6, 210/321.61, 321.87, 321.88, 321.89, 500.23, 210/502.1, 504; 436/161, 177, 178; 435/6; 427/244

See application file for complete search history.

(56) References Cited

U.S. PATENT DOCUMENTS

| 4,206,050 A | 6/1980 | Walch et al. |
| 4,960,692 A | 10/1990 | Kreft, III et al. |
| 5,124,041 A | 6/1992 | Sheer et al. |
| 5,139,668 A * | 8/1992 | Pan et al. ............... 210/321.8 |
| 5,240,994 A | 8/1993 | Brink et al. |
| 5,310,688 A * | 5/1994 | Zale et al. ............... 436/535 |
| 5,505,841 A | 4/1996 | Pirbazari et al. |
| 5,567,615 A * | 10/1996 | Degen et al. ............... 435/280 |
| 5,575,910 A | 11/1996 | Karbachsch et al. |
| 5,618,418 A | 4/1997 | Demmer et al. |
| 6,022,477 A * | 2/2000 | Luo et al. ............... 210/645 |
| 6,193,883 B1 * | 2/2001 | Kroner et al. ............ 210/198.2 |
| 6,550,622 B2 * | 4/2003 | Koslow ............... 210/490 |
| 6,780,327 B1 * | 8/2004 | Wu et al. ............... 210/660 |

FOREIGN PATENT DOCUMENTS

| CA | 1292952 | 12/1991 |
| EP | 0542855 | 11/1982 |
| EP | 0249932 A | 12/1987 |

(Continued)

OTHER PUBLICATIONS

Agrawal et al., Biotechnology and Bioengineering, 52, 539 (1996).

(Continued)

*Primary Examiner*—Joseph Drodge
(74) *Attorney, Agent, or Firm*—Klauber & Jackson LLC

(57) ABSTRACT

An apparatus and method for recovering bioproducts from a feed solution. In one embodiment, the apparatus includes a module housing, a membrane means disposed in the housing for filtering the bioproducts from the feed solution wherein a portion of the membrane means is coated with a polymeric coating, and an adsorbent bed disposed in the housing for retaining the bioproducts which permeate through the membrane, wherein the apparatus is adapted to allow fractionation and purification of the retained bioproducts from the bed by elution.

51 Claims, 16 Drawing Sheets

Configuration of the device containing membrane and adsorbent beads during filtration-cum-loading

FOREIGN PATENT DOCUMENTS

| | | |
|---|---|---|
| FR | 2510412 | 2/1983 |
| GB | 1526183 | 9/1978 |
| JP | 71-33290 | 5/1995 |
| WO | 94 09889 | 11/1994 |

OTHER PUBLICATIONS

Chang et al, Biotechnology and Bioengineering, 49, 204 (1996).
Freeman et al., Bio/Technology, 11, 1007 (1993).
Molinari et al., Biotechnology and Bioengineering, 36, 572 (1990).
Van Reis et al., Biotech. Bioengg., 38, 413 (1991).
Nigam et al., Biotech. Prog., 4(3):166 (1988).
Dai et al., Biotechnol. Prog. 15(12): 1095-1105 (1999).
Cadotte et al., J. Macromol. Sci. Chem., A15(5):727-755 (1981).
Aagesen et al., 1995, Gen. Eng. New, p-12, Apr. 1.
Agrawal et al., 1996, Biotech Bioengg., 52:539-48.
Belter et al., 1988. Bioseparations: Downstream Processing for Biotechnoogy, John Wiley & Sons, Inc.
Chang and Chase, 1996, Biotech. Bioengg., 49:204-16.
Darbre et al., Biochimica et Biophysica Acta, 1975, 393: 201-4.
Dickerson, 1969, The Structure and Action of Proteins, 44, 52, Harper and Row Publisher.
Freemann et al., 1993, Bio/Technology, 11:1007-12.
Hirayama et al., 1990, Biochem. Biophys. Res. Com., 173: 639-46.
Kaplan and Foster, 1971, Biochemistry, 10:630-6.
Lehninger, 1975, Biochemistry, 157, 162.
Longsworth et al., 1949, J. Phys. Colloid Chem., 53:126-35.
Molinari et al., 1990, Biotech. Bioengg., 36:572-80.
Nigam et al., 1988, Biotech. Prog., 4:166-72.
Radola, 1973, Biochimica et Biophysica Acta. 295:412-28.
Timesheff et al., 1980, J. Amer. Chem. Soc., 82:3157-61.
van Reis et al., 1991, Biotech. Bioengg., 38:413-22.
The Busy Researcher's Guide to Biomolecule Chromatography, 135, PerSpetive Biosystems, Inc., 1998.

* cited by examiner

Figure 1a. Configuration of the device containing membrane and adsorbent beads during filtration-cum-loading
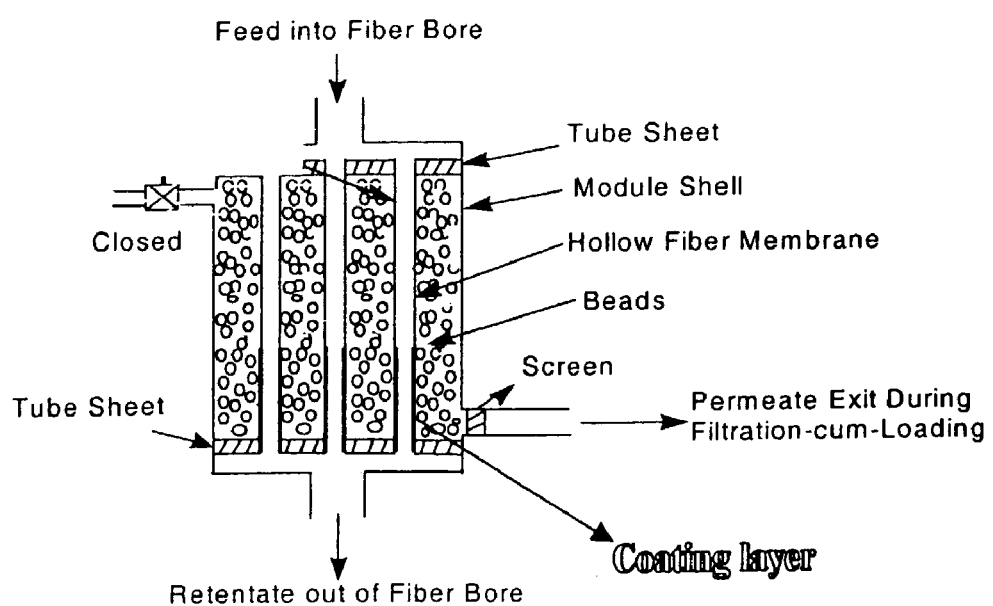

Figure 1b. Configuration of the device containing membrane and adsorbent beads during shell-side chromatographic elution.
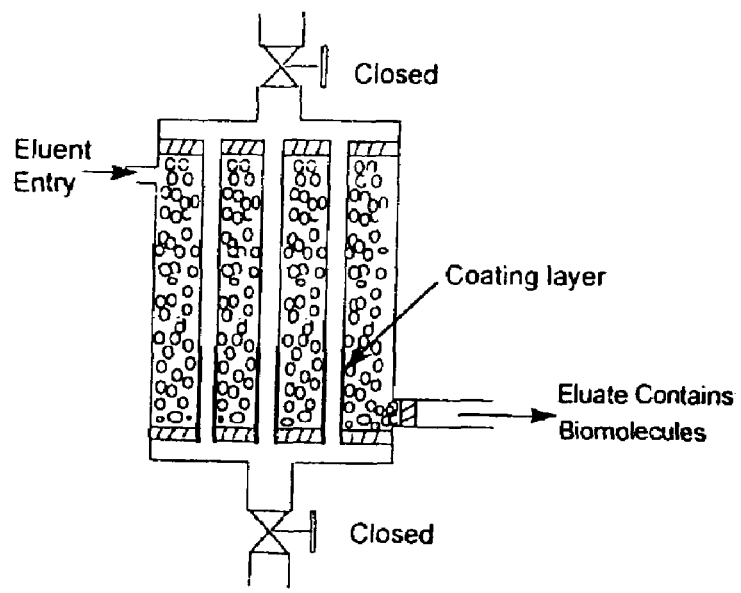

Figure 1C. Configuration of the device containing membrane and absorbent beads during tube-side chromatographic elution.
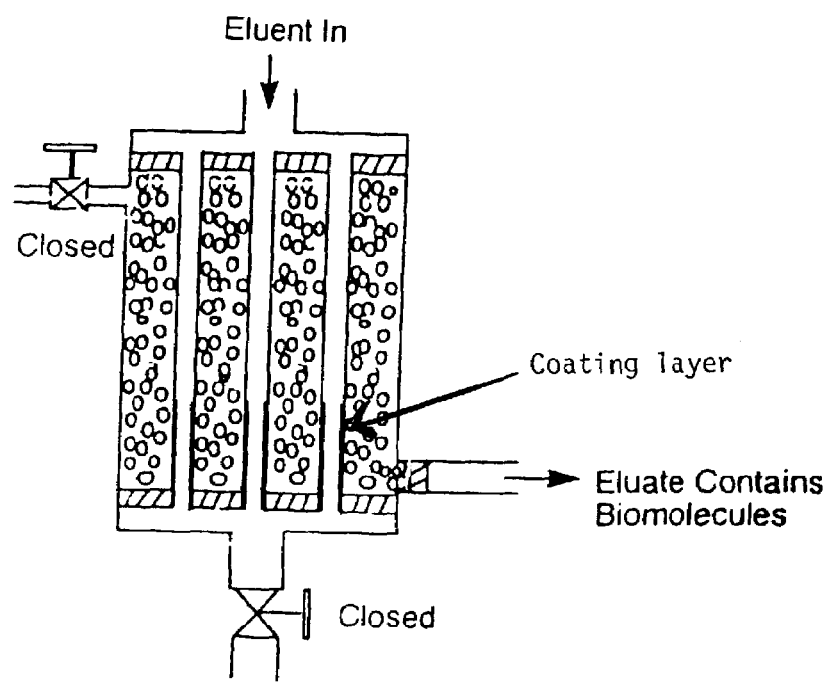

Figure 2a. Partial coating of the hollow fiber membranes by interfacial polymerization - concept of the partially coated hollow fiber membrane module in membrane filtration-cum-chromatography process and device.
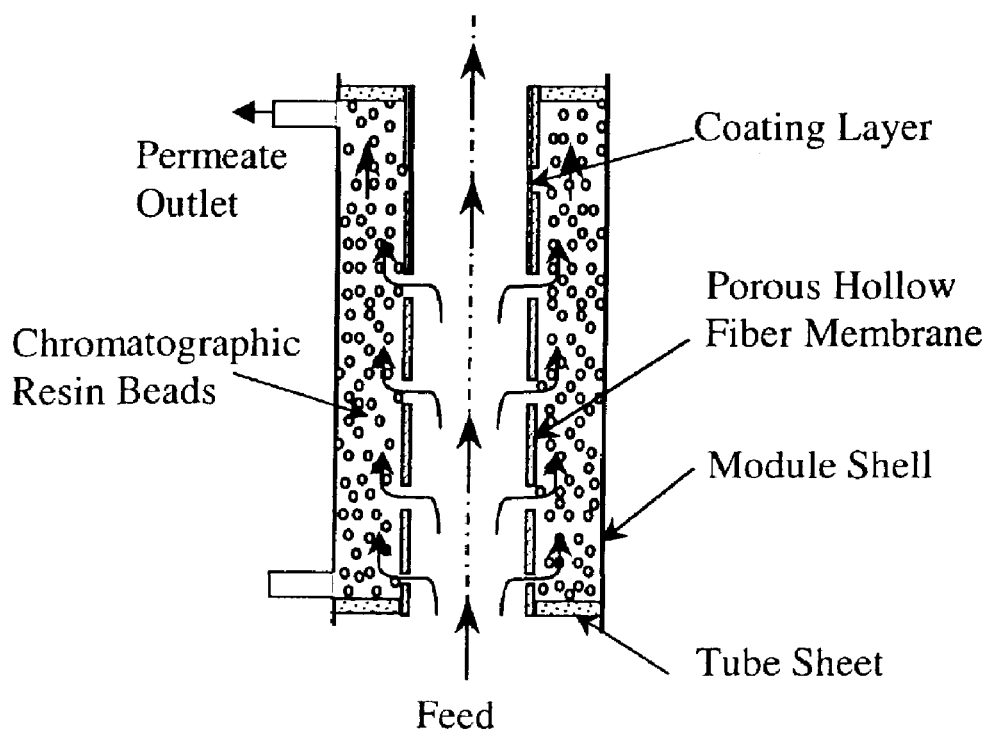

Figure 2b. Partial coating of the hollow fiber membranes by interfacial polymerization - device used to prepare the coating
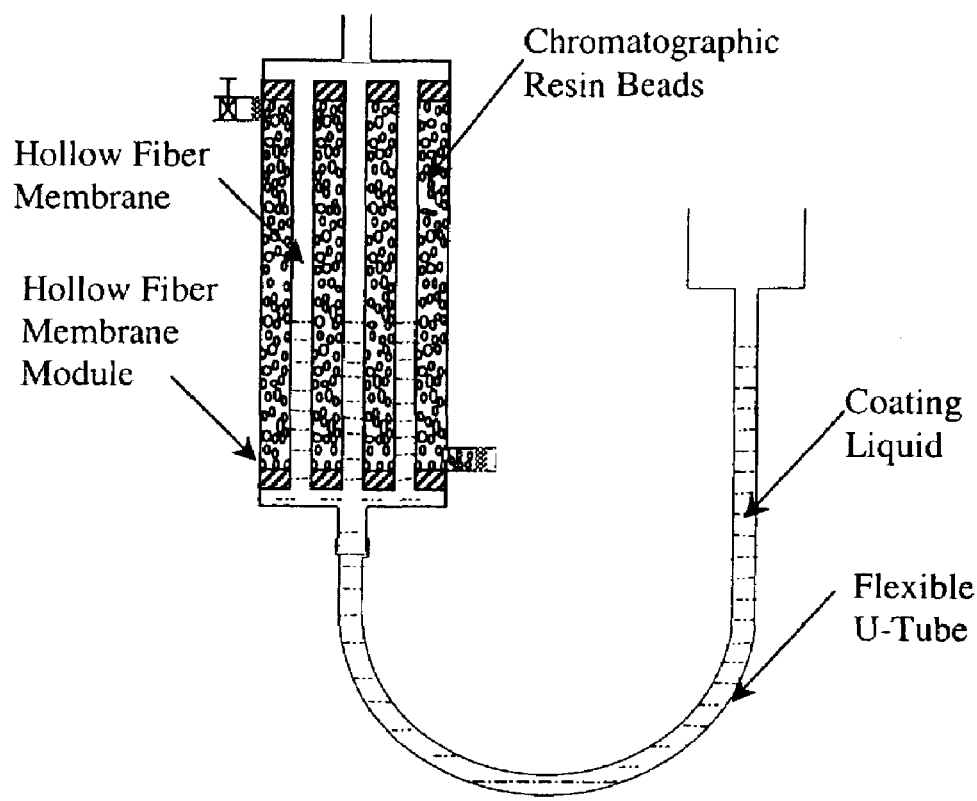

Figure 3. Schematic of the membrane filtration-cum-chromatography setup.
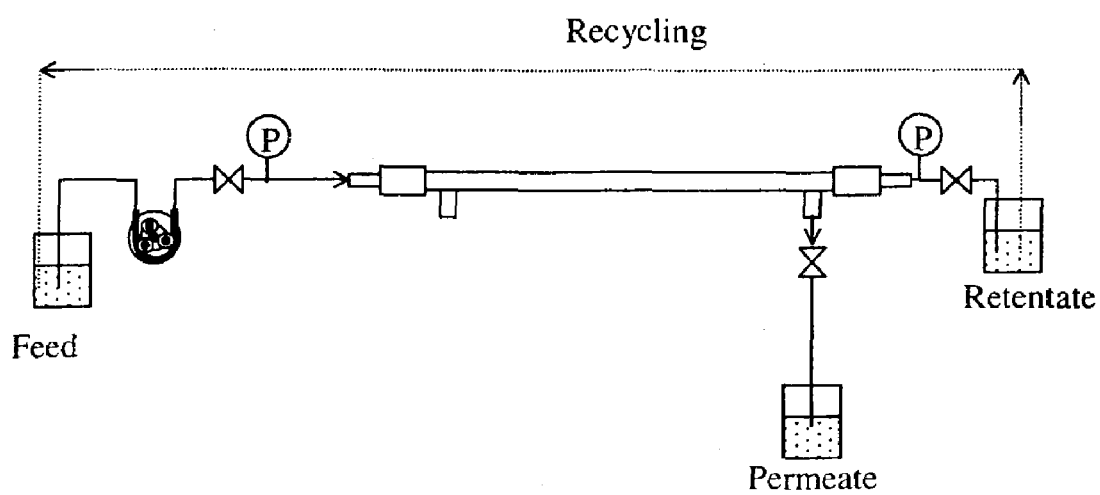

Figure 4. Comparison of Mb breakthrough results between the uncoated module and the partially coated module.
Feed: $C_{Mb}$ 250 µg/ml, flow rate 200 ml/min, pressure 5 psig (34.5 KPag)
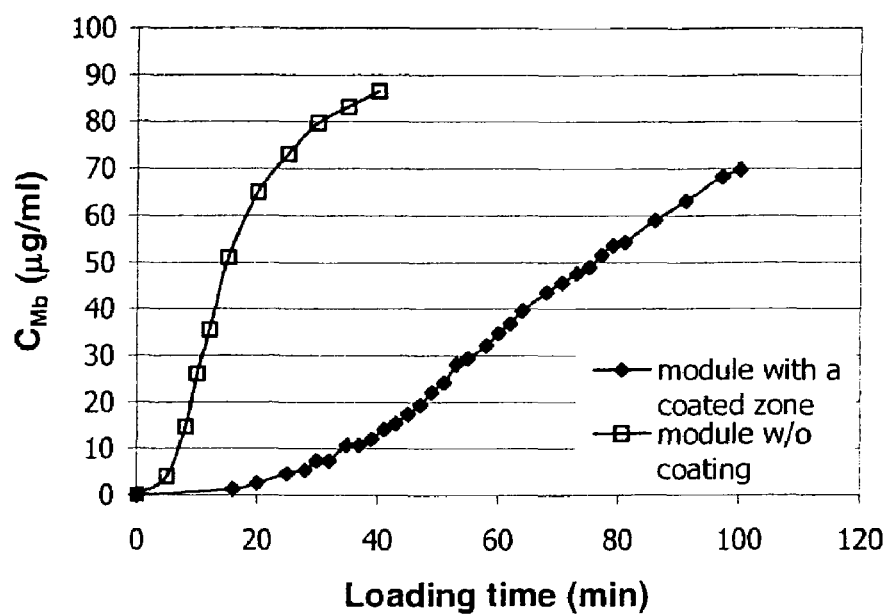

Figure 5a. Comparison of Mb/α-LA separation behaviors at similar loading conditions - before coating, total protein loaded: Mb 3.25 mg, α-LA 1.59 mg.
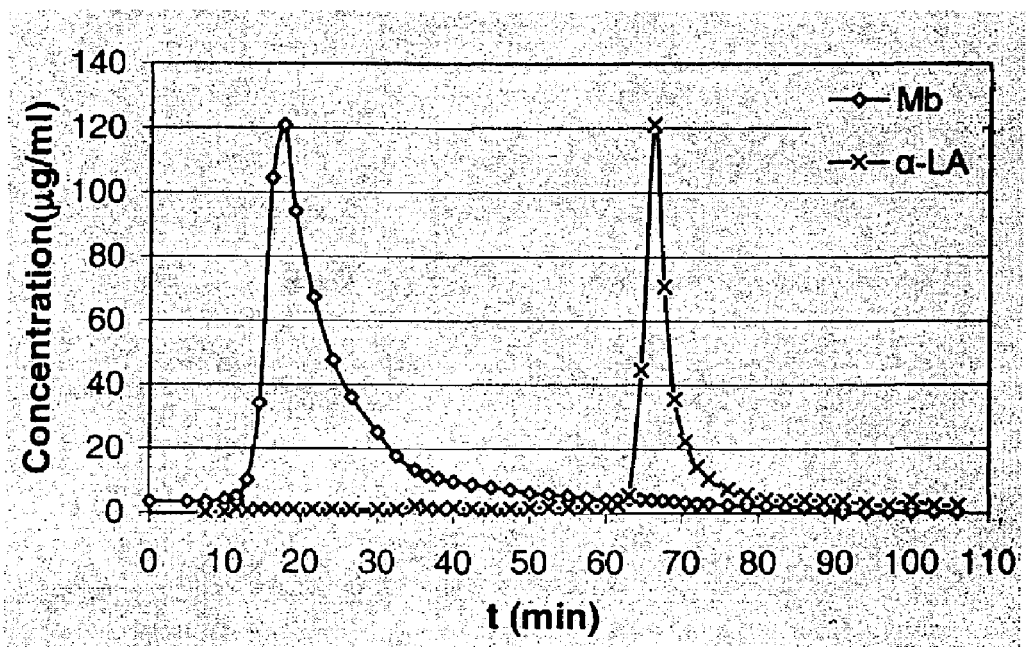

Figure 5b. Comparison of Mb/α-LA separation behaviors at similar loading conditions - after coating, total protein loaded: Mb 3.08 mg; α-LA 2.28 mg.
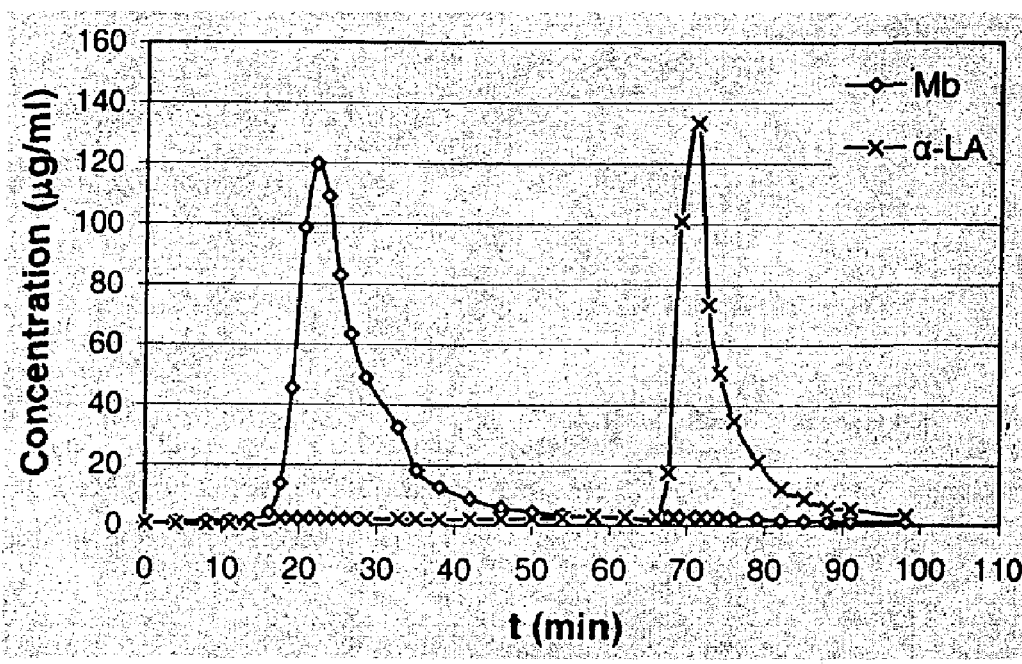

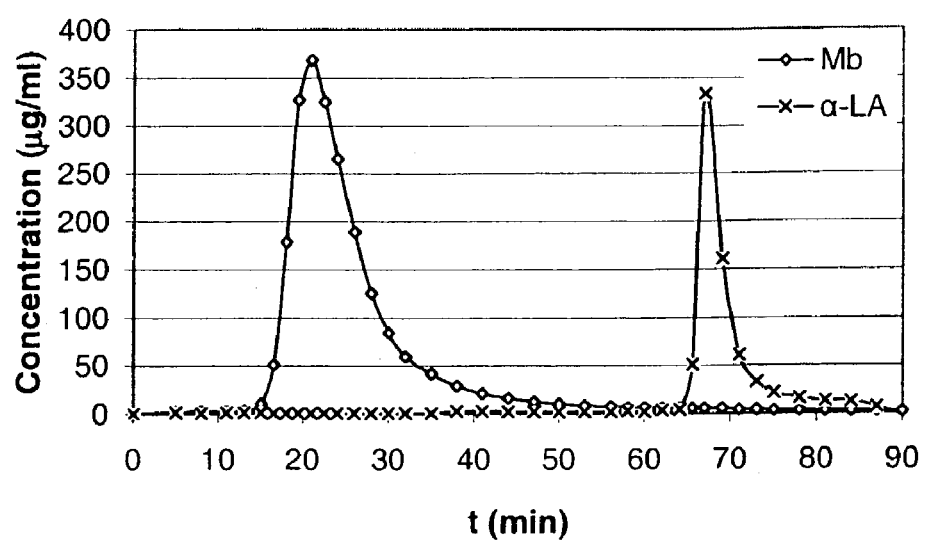
Figure 6a. Loading capacity enhancement in the module having a coated zone - longer loading time; total protein loaded: Mb 9.56 mg, α-LA 3.47 mg.

Figure 6b. Loading capacity enhancement in the module having a coated zone - higher loading concentration; total protein loaded: Mb23 mg, α-LA 11.9 mg.
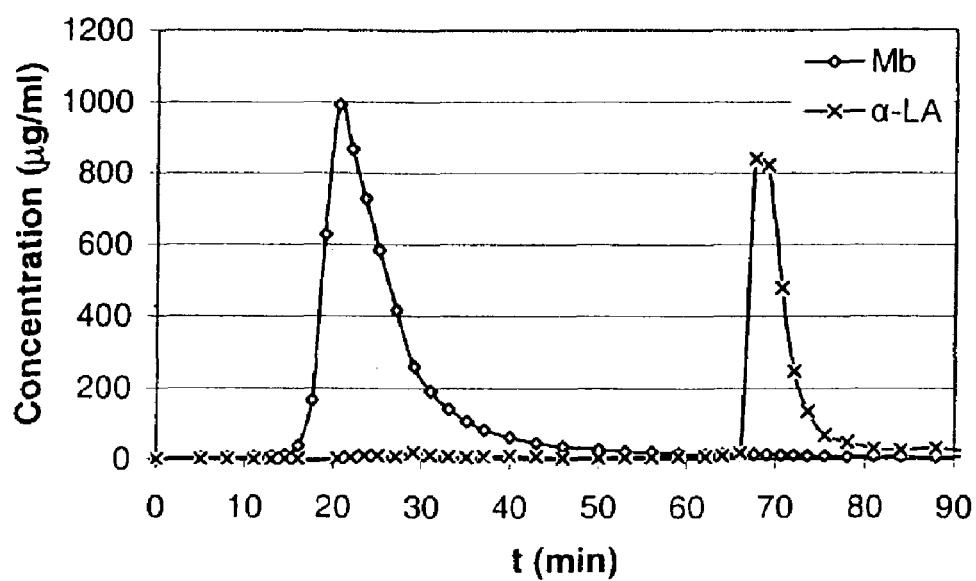

Figure 7a. Comparison of Mb/BSA loading capacities between the uncoated module and the module with a coated zone - before coating, total protein loaded: Mb 4.19 mg, BSA 1.61 mg.
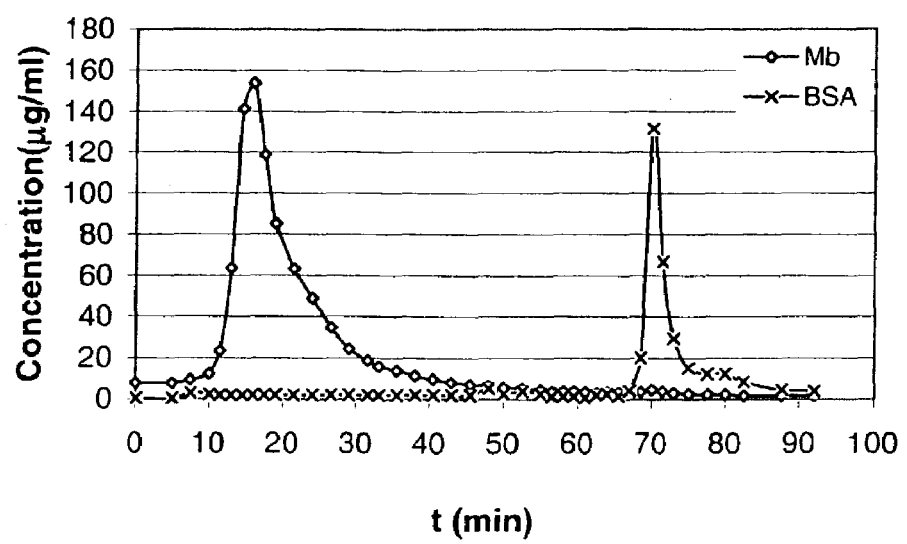

Figure 7b. Comparison of Mb/BSA loading capacities between the uncoated module and the module with a coated zone - after coating, total protein loaded: MB 9.14 mg; BSA 3.36 mg.
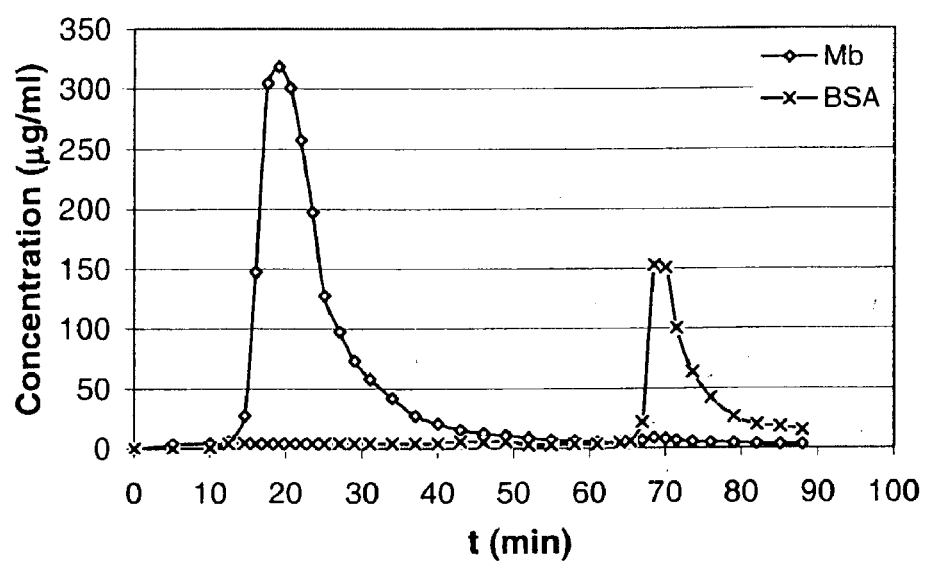

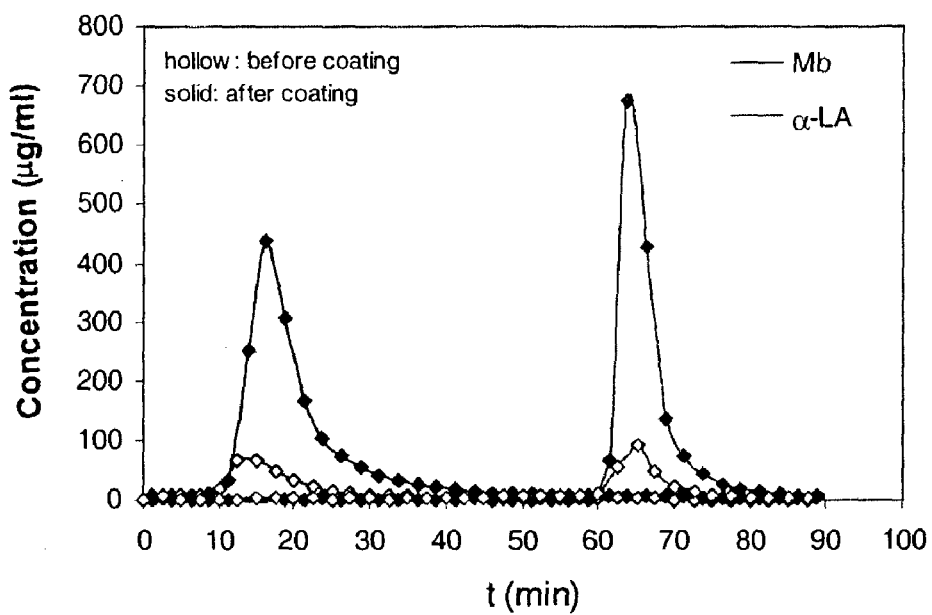
Figure 8. Effect of coating on Mb/α-LA separation for a MF cartridge
Feed: 50 µg/ml of Mb and α-LA solution in 20 mM Tris- pH 8.5
Loading: 5 psig, 4 min before coating, 29 min after coating
Elution: FR: 2.5 ml/min; 0-50 min 0.05 M NaCl , 50-90 min 0.5M NaCl in Tris pH 8.5.

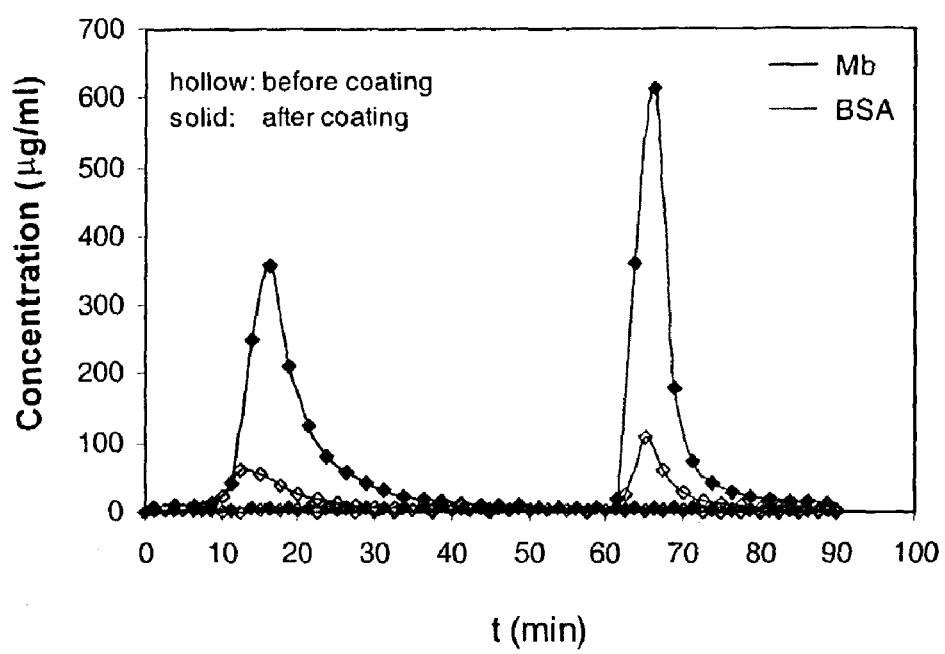
Figure 9. Effect of coating on Mb/BSA separation for a MF cartridge
    Feed: 50 µg/ml of Mb and BSA solution in 20 mM Tris- pH 8.5
    Loading: 200 ml/min, 5 psig, 4 min before coating, 25 min after coating
    Elution: FR: 2.5 ml/min; 0-50 min 0.05 M NaCl , 50-90 min 0.5M NaCl in Tris pH 8.5.

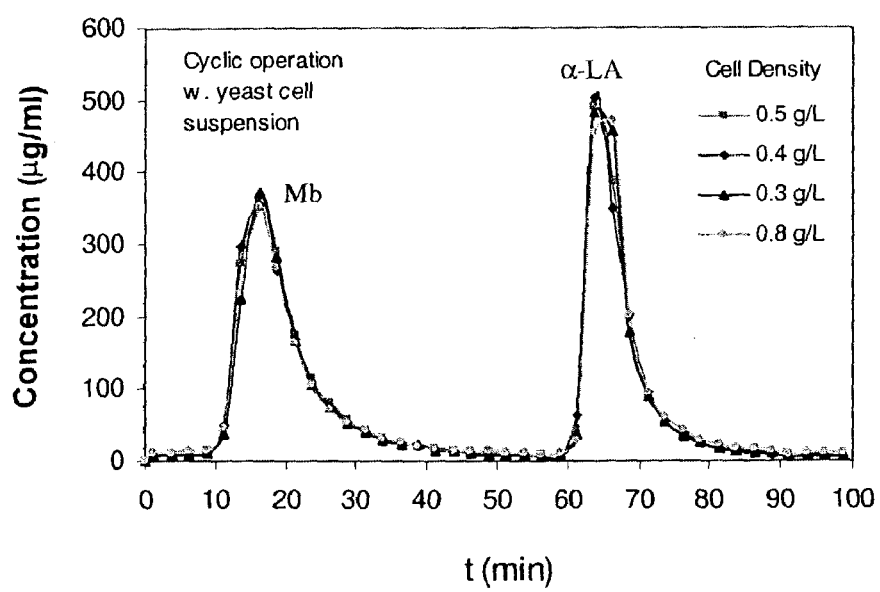
Figure 10. Cyclic runs for Mb/α-LA separation from synthetic yeast broths of different cell densities.
Feed: 50 μg/ml of Mb and α-LA yeast cell suspension
Loading: 5 psig, 29 min
Elution: FR: 2.5 ml/min; 0-50 min 0.05 M NaCl, 50-100 min 0.5M NaCl in Tris pH 8.5.

METHOD AND APPARATUS FOR ISOLATION AND PURIFICATION OF BIOMOLECULES

This application claims the benefit of Provisional Application No. 60/379,477, filed May 10, 2002.

FIELD OF THE INVENTION

The present invention relates to bioproduct or biomolecule separation generally and, more particularly, but not by way of limitation, to a novel method and apparatus for isolating and purifying biomolecules by membranes and adsorbents.

BACKGROUND OF THE INVENTION

Innovations in and improvement of bio-downstream processing, which is responsible for about 50–80% of the cost of recombinant proteins and other biomolecules, play a very important role in increasing the yield and reducing the cost of biopharmaceutical production. Biomolecule isolation and purification from a fermentation broth usually involve centrifugation, filtration, adsorption, and chromatography steps. Each step contributes to the product cost and product loss.

Bioproduct recovery from fermentation broths is complicated by the large number of dissolved substances and suspended particles present in the broth. Most bioseparation processes involve the following steps: removal of insolubles by either filtration or centrifugation, isolation of products using either adsorption or solvent extraction, purification (via chromatography and precipitation) and polishing via crystallization, or spray drying and lyophilization. For intracellular products, cell disruption is also needed to release the product before the removal of insolubles. See: Belter, P. A., Cussler, E. L. and Hu, W. Bioseparations: Downstream Processing for Biotechnology, John Wiley & Sons, Inc. (1988). Although the series of separation steps can usually accomplish the product recovery, reduction in the overall number of separation operations is desirable because of the low product yields associated with some steps. The development of techniques that reduce the overall number of steps are gaining popularity due to their reduced cost, increased yield and productivity along with the reduction in the complexity of the downstream processing flowsheets. See: Agrawal, A. and Burns, M. A., Biotechnology and Bioengineering, 52, 539 (1996); Chang, Y. K. and Chase, H. A., Biotechnology and Bioengineering, 49, 204 (1996); Freeman, A., Woodley, J. M. and Lilly, M. D., Bio/Technology, 11, 1007 (1993); and Molinari, R., Torres, J. L., Michaels, A. S., Kilpatrick, P. K. and Carbonell, R. G., Biotechnology and Bioengineering, 36, 572 (1990).

Biomolecules (e.g., interferons, hormones, immunoglobulins, growth factors, DNAs, etc.) obtained from large-scale fermentation and cell-culture processes may be present in low concentrations in a complex medium/broth containing various combinations of cells, cell fragments, lysed cells, colloidal materials, etc. For example, the medium may be a mixture of an aqueous solution and particles. By way of another example, the medium could be proteins dissolved in water. The nature of such heterogeneous aqueous solutions containing the biomolecules is influenced by the nature of the bioproduct, i.e., whether the product is extracellular or intracellular. In the case of intracellular products, cells are recovered from the broth; then cell lysis and homogenization are undertaken to produce a homogenate. The biomolecules are next separated from the cell debris by lysate clarification. In the case of extracellular products, the biomolecules are separated from the whole cells by clarification.

A number of different technologies or sequence of technologies can be employed to eliminate the cellular and colloidal material prior to bioproduct purification via adsorption/chromatography steps. These include centrifugation, flocculation, liquid-liquid extraction and various forms of microfiltration (dead-end, tangential flow and rotary). The devices involved in these processes are complex; there is significant loss of product at each step. See: van Reis, R., Leonard, L. C., Hsu, C. C. and Builder, S. E., Industrial scale harvest of proteins from mammalian cell culture by tangential flow filtration, Biotech. Bioengg., 38, 413 (1991). It would be of great use if there were a process and an apparatus to recover and purify the product biomolecule from the whole broth (for extracellular products) or a homogenate (for intracellular products) in one step.

Toward this one-step approach, three solutions have been suggested which employ specialized adsorbent beads/particles.

Nigam et al. (1988) have suggested using specially prepared immobilized adsorbents consisting of small, porous adsorbent particles entrapped within a reversible hydrogel matrix which excludes colloidal contaminants and suspended solids. See: Nigam, S. C., Sakoda, A. and Wang, H. Y., Bioproduct recovery from unclarified broths and homogenates using immobilized adsorbents, Biotech. Prog., 4(3), 166 (1988).

Chang and Chase (1996) have employed "streamline" adsorbents specially designed by Pharmacia Biotech (Uppsala, Sweden) for use in expanded bed adsorption of biomolecules from unclarified feedstocks. See Chang, Y. K. and Chase, H. A., Ion exchange purification of G6PDH from unclarified yeast cell-homogenates using expanded bed adsorption, Biotech. Bioengg., 49, 402 (1996).

Aagesen et al. (1995) have designed beads incorporating dense inert particles so that they have a significantly higher density and can settle easily from an expanded fluidized bed after adsorbing the protein of interest from the solution; this technique has been identified as upfront chromatography (UFC) and the beads are identified as UpFront matrix. See: Aagesen, M., Wickborg, T. and Lihme, A., Single-step initial protein purification with UpFront Chromatography, Gen. Eng. News, p-12, Apr. 1, 1995.

All of these aforementioned techniques require specially designed and costly adsorbents and/or unusual operational conditions in expanded/fluidized beds to accommodate the presence of an unclarified broth. More often than not, the specially designed bead may not have the required ion exchange or other ligands for the biomolecule separation from solution. Further, the beads become contaminated with cell fragments which will contaminate the bioproduct during elution. On the other hand, microfiltration-based cell-protein separation or lysate clarification are being increasingly employed in small as well as large-scale harvesting of proteins and other biomolecules. Cf. van Reis et al. (1991), supra. Further, a wide variety of adsorbent beads or chromatographic matrix particles are commercially available and routinely used for biomolecule purification.

An object of the present invention is to efficiently integrate these functions into one device using commercially available and commonly utilized microfiltration membranes and adsorbent beads.

Various bioseparation-type devices have been proposed.

One type of device employs an adsorption bed with a hollow fiber housing, wherein a hollow fiber module was used as a housing for adsorbent beads, as described by Pan and McMinis in their U.S. Pat. No. 5,139,668 (1992), wherein adsorbent beads were "emplaced" on the tube side of the hollow fiber module, or, in another case, on the shell side of the module. The device was intended for gas or liquid separations and thus represented certain advantages over conventional packed bed elements or columns, including: the fluid pressure drop through the element is independent of the size of the particles because the fluid flow path through the fiber bore is separated from the particles in the case of particles on the shell side; very fine particles can, therefore, be used on the shell side; the microporous hollow fibers provide efficient and uniform contact between the adsorbent particles and the fluid mixture for a wide range of flow rates, etc. Thus, the hollow fiber modules provided a better housing for some adsorbent beads for certain applications as compared to the conventional packed bed adsorption columns. Notably, however, the hollow fibers were only used as the housing for adsorbent particles and the fibers themselves did not play any role in the separation. Further, no flow stream was ever taken out through the particle side. Also, the use of a polymeric coating on part of the length of the hollow fibers as provided in the present invention is neither disclosed nor suggested by this reference.

Another approach to bioseparation involved the simultaneous ultrafiltration (UF) and affinity sorptive separation of proteins in a hollow fiber membrane module as reported by Molinari, R., Torres, J. L., Michaels, A. S., Kilpatrick P. K. and Carbonell, R. G. in "Simultaneous Ultrafiltration and Affinity Sorptive Separation of Proteins in a Hollow Fiber Membrane Module," Biotechnol. Bioeng., 36, 572 (1990), wherein sorptive gel particles were loaded into the shell side of a hollow fiber membrane module, and the device was used in a process for simultaneous protein ultrafiltration and adsorption. In the process of Molinari et al., long binding times (seven hours in the example of horse serum cholinesterase, and five hours in the example of bovine liver carboxylesterase) were used to load proteins onto the adsorbent particles by recirculating the retentate, while the proteins were always present in the filtrate. At the end of the loading step, breakthrough occurred and the adsorbent bed was completely saturated by the protein. Furthermore, in the process of Molinari et al., the elution was conducted by permeating an eluent through the fiber lumen into the shell space. Since the bed was saturated by the feed protein, the desorption was similar to that in a conventional batch adsorption process. No chromatographic purification or fractionation took place.

However, in the present invention, as discussed herein, the mode of operation of the inventive device/process is appropriate for chromatographic fractionation of proteins through a bed of absorbents. Moreover, Molinari et al. neither disclose nor suggests a polymeric coating on part of the length of the hollow fibers as utilized in the present invention.

Yet another type of device and process for bioseparation involves moving adsorbent particles through the lumen of membrane filters, wherein adsorbent particles binding the target compound are circulated through the lumen of a tubular microfiltration membrane or the lumen of a hollow fiber membrane module. The separation occurs when the compound bound to the particles is retained together with the particles and the compound not bound to the particles permeates through the membrane. This type of device and process were described in three patents by Byers et al., Canadian Patent 1,292,952 (1991), Degen et al., U.S. Pat. No. 5,567,615 (1996), and Pirbazari and Badriyha, U.S. Pat. No. 5,505,841 (1996) respectively. While the former two patents were aimed at biomolecule separations, the third was directed toward water decontamination. In Byers et al. (1991), for example, adsorbent beads were added to a mixture consisting of the target biomolecule and impurities, and the resulting solution was mixed to allow the adsorption of the target biomolecule onto the beads. The suspension was then circulated through the lumen of hollow fiber membranes. The target biomolecule was retained with the beads due to the large size of the beads. The impurities which were not bound to the beads permeated through the membrane to the shell space. None of these references either disclose or suggest the use of a polymeric coating as provided by the present invention.

Dai, X. P. et al., "An integrated process for biomolecule isolation and purification," Biotechnol. Prog. 15 (12), 1095–1105 (1999) and Luo, R. G. and Sirkar, K. K., U.S. Pat. No. 6,022,477 (2000) disclose the use of chromatographic resin beads on the shell side of a ultrafiltration/microfiltration membrane device. However, the references do not disclose or suggest a polymeric coating on part of the length of the hollow fiber as utilized by the present invention.

Cadotte, J. E., Interfacially Synthesized Reverse Osmosis Membrane, U.S. Pat. No. 4,277,344 (1981) and Cadotte, J. E., King, R. S., Majerle, R. J. and Petersen, R. J., Interfacial synthesis in the preparation of reverse osmosis membranes, J. Macromol. Sci.-Chem., A15 (5), pp. 727–755 (1981) describe the use of interfacial polymerization to prepare reverse osmosis membranes. However, these references do not contemplate the purification of biomolecules as provided by the present invention.

A principal object of the present invention is to provide a method and device for the isolation and purification of biomolecules.

Another object of the present invention is to provide a method and apparatus which integrate clarification, concentration and separation of biomolecules into a single step or single device.

It is another object of the present invention to provide an apparatus and method which may be easily adopted for large scale processing.

Another object is to provide a hybrid bioseparation apparatus and process involving commercially available membranes and adsorbents.

A further object is to provide a bioseparation method and apparatus suitable for both extracellular and intracellular products.

An additional object of the present invention is to provide a bioseparation method and apparatus such that the capacity of biomolecule adsorption using commercially available adsorbent is increased and the pressure drops which reduce the permeate flow rate are minimized.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing a novel method and apparatus for isolating and purifying biomolecules by membranes and adsorbents.

In one aspect, the present invention relates to a membrane module means for recovering bioproducts from a feed solution, the means comprising a module housing, membrane means disposed in the housing for filtering the bioproducts from the feed solution wherein a portion of the feed side of the membrane means is coated with a polymeric coating so as to render such portion impermeable to the bioproducts to be recovered, and an adsorbent bed means disposed in the housing for retaining the bioproducts which permeate through the membrane means, wherein the membrane module means is adapted to allow fractionation and purification of the retained bioproducts from the bed by elution or other chromatographic techniques.

The polymeric coating may be partially permeable or essentially impermeable to water. However, it should be essentially impermeable to water under the applied pressure difference employed with the membrane means used. The polymeric coating should also be impermeable to the biomolecule to be isolated and purified. It is preferred that the polymeric coating be essentially impermeable to water under the operating conditions.

The polymeric coating can be composed of any polymeric substance which does not destabilize the structure of the membrane means during application of the polymeric coating. Polymeric substances which can be utilized include, for example, polyamides, polysulfones, polyethersulfones, aromatic polyamides, polyvinyl alcohols, polyvinylidene fluorides, polyethyleneimines, polyureas, polydimethylsiloxanes, polyacrylonitriles and the like.

The portion of the membrane means which is coated with the polymeric coating should be positioned so as to substantially reduce the leakage of the biomolecules to be isolated and purified from the shell side permeate outlet over the length of time used to load the biomolecules. Preferably, the portion of the membrane which is coated with the polymeric coating is located at the bottom of the membrane means close to the shell side permeate outlet. The portion of the membrane means which is coated with the polymeric coating should constitute about one-sixteenth to about one-half of the membrane means, with about one-quarter being preferred.

Various methods known in the art can be employed to apply the polymeric coating to the membrane means. For example, the polymeric coating can be physically adhered to the membrane means. It is preferred that the polymeric coating be applied using interfacial polymerization.

The present invention also relates to an apparatus for recovering bioproducts from a feed solution, wherein the apparatus comprises: a housing having a feed inlet means, a feed outlet means, and a permeate outlet means; at least one membrane means disposed within the housing and having a feed side and a permeate side wherein a portion of the feed side of the membrane means is coated with a polymeric coating so as to render such portion impermeable to the bioproduct to be recovered; and a packed bed of adsorbent particles disposed within the housing in contact with the permeate side of the membrane means. The feed inlet means allows the feed solution to pass into contact with the feed side of the membrane. The bioproducts are separated from the feed solution by permeation to the permeate side of the membrane means, and the permeated bioproducts contact the beads in the packed bed. The bioproducts are retained by the adsorbent particles. Thus, the bioproducts are isolated from the feed solution.

In another aspect, the present invention relates to a method of recovering bioproducts from a feed solution, wherein the method comprises: providing a membrane module comprising a housing, at least one membrane means disposed within the housing and having a feed side and a permeate side wherein a portion of the feed side of the membrane means is coated with a polymeric coating so as to render such portion impermeable to the bioproducts to be recovered, and a packed bed of adsorbent particles disposed within the housing in contact with the permeate side of the membrane means; passing the feed solution into the Membrane module to contact the feed side of the membrane; and separating bioproducts from the feed solution by permeation through to the permeate side of the membrane means and allowing the permeated bioproducts to contact the adsorbent particles, wherein the bioproducts are retained by the adsorbent particles, whereby the bioproducts are isolated from the feed solution.

BRIEF DESCRIPTION OF THE DRAWINGS

Understanding of the present invention and the various aspects thereof will be facilitated by reference to the accompanying drawing figures, submitted for purposes of illustration only and not intended to limit the scope of the invention, in which:

FIG. 1a is a cross-sectional elevational illustrative view of a preferred embodiment during filtration-cum-feeding in chromatographic separation, in accordance with the present invention;

FIG. 1b is the preferred embodiment of FIG. 1a during shell-side elution in chromatography, in accordance with the present invention;

FIG. 1c is the preferred embodiment of FIG. 1a during tube-side elution in chromatography, in accordance with the present invention;

FIG. 2a is a cross-sectional view of a preferred embodiment illustrating the concept of the partially coated hollow fiber membrane filtration-cum-chromatography device, in accordance with the present invention;

FIG. 2b is a cross-sectional view of a preferred embodiment showing the concept of partial coating of the hollow fiber membrane by interfacial polymerization and a coating device;

FIG. 3 is a schematic showing the experimental setup used in the cleaning, loading, elution and washing steps;

FIG. 4 graphically compares myoglobin breakthrough results using a partially coated module of the present invention and an uncoated module;

FIG. 5a graphically illustrates a tube side elution profile for the separation of myoglobin and α-lactalbumin using an uncoated module;

FIG. 5b graphically illustrates a tube side elution profile for the separation of myoglobin and α-lactalbumin using a partially coated module;

FIG. 6a graphically illustrates a tube side elution profile for the separation of myoglobin and α-lactalbumin using a partially coated module and a longer loading time as compared to FIG. 5b;

FIG. 6b graphically illustrates a tube side elution profile for the separation of myoglobin and α-lactalbumin using a partially coated module at a higher protein loading concentration as compared to FIG. 5b;

FIG. 7a graphically illustrates a tube side elution profile for the separation of myoglobin and bovine serum albumin using an uncoated module; and FIG. 7b graphically illustrates a tube side elution profile for the separation of myoglobin and bovine serum albumin using a partially coated module.

FIG. 8 graphically illustrates the side elution profile for the separation of myoglobin and α-lactalbumin with and without coating of the module.

FIG. 9 graphically illustrates the side elution profile for the separation of myoglobin and Bovine Serum Albumin with and without coating of the module.

FIG. 10 is a side elution profile for the separation of myoalobin and α-lactalbumin using four loading-elution-regeneration based cyclic runs with a synthetic yeast fermentation broth feed without cleaning between runs.

DETAILED DESCRIPTION OF THE PREFERRED EMBODIMENTS

In one aspect, the present invention relates to a membrane module means for recovering bioproducts from a feed solution, the means comprising a module housing, membrane means disposed in the housing for filtering the bioproducts from the feed solution wherein a portion of the feed side of the membrane means is coated with a polymeric coating so as to render such portion impermeable to the bioproduct to be recovered, and an adsorbent bed means disposed in the housing for retaining the bioproducts which permeate through the membrane means, wherein the membrane module means is adapted to allow fractionation and purification of the retained bioproducts from the bed by elution.

The present invention also contemplates a system comprising a plurality of such membrane module means. In one embodiment, for example, the system may include at least two of the modules are connected in parallel.

The present invention also relates to an apparatus for recovering bioproducts from a feed solution, wherein the apparatus comprises: a housing having a feed inlet means, a feed outlet means, and a permeate outlet means; at least one membrane means disposed within the housing and having a feed side and a permeate side wherein a portion of the feed side of the membrane means is coated with a polymeric coating so as to render such portion impermeable to the bioproduct to be purified; and a packed bed of adsorbent particles disposed within the housing in contact with the permeate side of the membrane. The feed inlet means allows the feed solution to pass into contact with the feed side of the membrane. The bioproducts are separated from the feed solution by permeation to the permeate side of the membrane means, and the permeated bioproducts contact the packed bed. The bioproducts are retained by the adsorbent particles. Thus, the bioproducts are isolated from the feed solution.

The polymeric coating may be partially permeable or essentially impermeable to water. However, it should be essentially impermeable to water under the applied pressure difference employed with the membrane means used. The polymeric coating should also be impermeable to the biomolecule to be isolated and purified. It is preferred that the polymeric coating be essentially impermeable to water.

The polymeric coating can be composed of any polymeric substance which does not destabilize the structure of the membrane means during application of the polymeric coating. Polymeric substances which can be utilized include, for example, polyamides, polysulfones, aromatic polyamides, polyvinyl alcohols, polyethersulfones, polyethyleneimines, polydimethylsiloxanes, polyacrylonitriles, polyureas, polyvinylidene fluorides and the like.

The portion of the membrane means which is coated with the polymeric coating should be positioned so as to substantially reduce the leakage of the biomolecules to be isolated and purified from the shell-side permeate outlet over the length of time used to load the biomolecules. Preferably, the portion of the membrane which is coated with the polymeric coating is located at the bottom of the membrane means close to the shell side permeate outlet. The portion of the membrane means which is coated with the polymeric coating should constitute about one-sixteenth to about one-half of the membrane means, with about one-quarter being preferred.

Various methods known in the art can be employed to apply the polymeric coating to the membrane means. For example, the polymeric coating can be physically adhered to the membrane means. It is preferred that the polymeric coating be applied using interfacial polymerization.

The apparatus may further include means to control the inlet flow of the feed solution. Thus, the introduction of feed solution into the feed inlet means may be terminated before the packed bed becomes saturated, or the introduction of feed solution into the feed inlet may be terminated before breakthrough of the bioproducts occurs at the feed outlet means.

The bioproducts retained by the adsorbent particles are preferably capable of being eluted directly from the apparatus. Thus, in one embodiment, the housing is adapted to allow introduction of an elution solution, wherein the bioproducts are capable of being purified in situ by passing the elution solution over the adsorbent particles disposed in the membrane module. In another embodiment, the apparatus is adapted to allow an elution solution to pass through the membrane and into contact with the adsorbent particles in order to elute and purify the retained bioproducts.

In a preferred embodiment, the adsorbent particles are chromatographic matrix particles. The adsorbent particles may be adsorbent beads. In a particular embodiment, the adsorbent particles have an effective diameter of 5 micrometers or greater. In general, the adsorbent particles may be any which are useful for the separation of biomolecules, including, for example, anion exchangers, cation exchangers, hydrophilic and reverse phase adsorbents, immunoadsorbents, protein A/G and the like.

The adsorbent particles may also comprise affinity ligands attached thereto.

The adsorbent particles preferably reduce the differences in transmembrane pressure along the length of the feed solution flow path between the feed inlet means and the feed outlet means.

The membrane means can utilize any membrane which is not destabilized by the polymeric coating and which allows the biomolecules which are to be fractionated and purified to pass through the membrane, but not undesirable materials such as suspended particles.

In one preferred embodiment, the membrane means is a microfiltration membrane wherein a portion of the feed side of the microfiltration membrane is coated with a polymeric coating. In another preferred embodiment, the membrane means is an ultrafiltration membrane wherein a portion of the feed side of the ultrafiltration membrane is coated with a polymeric coating.

In a preferred embodiment, the apparatus is a hollow fiber membrane module having at least one hollow fiber. Further preferably, a plurality of hollow fibers are provided in a module.

In the hollow fiber membrane module, the adsorbent particles are disposed on the shell side of the hollow fiber, and the feed solution is passed through the tube side of the hollow fiber.

The module is preferably provided with a permeate-side inlet means and a permeate-side outlet means.

The hollow fiber preferably has an inner diameter in the range of 100 micrometer to 2000 micrometer.

In another preferred embodiment, the membrane module is a plate-and-frame membrane module.

In another aspect, the present invention relates to a method of recovering bioproducts from a feed solution, wherein the method comprises: providing a membrane module comprising a housing, at least one membrane means disposed within the housing and having a feed side and a permeate side wherein a portion of the feed side of the membrane means is coated with a polymeric coating so as to render such portion impermeable to the bioproducts to be recovered, and a packed bed of adsorbent particles disposed within the housing in contact with the permeate side of the membrane; passing the feed solution into the membrane module to contact the feed side of the membrane; and separating bioproducts from the feed solution by permeation through to the permeate side of the membrane and allowing the permeated bioproducts to contact the adsorbent particles, wherein the bioproducts are retained by the adsorbent particles, whereby the bioproducts are isolated from the feed solution.

In one preferred embodiment, the introduction of feed solution into the membrane module is terminated before the packed bed becomes saturated.

In another preferred embodiment, the introduction of feed solution into the membrane module is terminated before breakthrough of the bioproducts occurs at the feed outlet of the membrane module.

The method further preferably includes eluting the bioproducts retained by the adsorbent particles disposed in the membrane module.

In a preferred embodiment, the method includes purifying the bioproducts by passing an elution solution over the adsorbent particles disposed in the membrane module.

In one embodiment, an elution solution may be passed through the membrane means and into contact with the adsorbent particles in order to purify the retained bioproducts.

In general, the adsorbent particles may be any which are useful for the separation of biomolecules, including, for example, anion exchangers, cation exchangers, hydrophobic and reverse phase adsorbents, immunoadsorbents, protein A/G and the like.

The method may be practiced with adsorbent particles which are chromatographic matrix particles.

The method may be practiced with adsorbent particles which are adsorbent beads.

The adsorbent particles may have an effective diameter of 5 micrometers or greater.

The adsorbent particles may further include affinity ligands attached thereto.

Preferably, the adsorbent particles reduce the differences in transmembrane pressure along the length of the feed solution flow path through the module.

The membrane means can utilize any membrane which is not destabilized by the polymeric coating and which allows the biomolecule to be fractionated and purified to pass through the membrane but not undesirable materials such as suspended particles.

In one preferred embodiment of the method, the membrane is a microfiltration membrane wherein a portion of the feed side of the microfiltration membrane is coated with a polymeric coating. In another preferred embodiment, the membrane is an ultrafiltration membrane wherein a portion of the feed side of the ultrafiltration membrane is coated with a polymeric coating.

In one preferred configuration, the membrane module is a hollow fiber membrane module having at least one hollow fiber. The adsorbent particles are preferably disposed on the shell side of the hollow fiber, and the feed solution is passed through the tube side of the hollow fiber. The hollow fiber preferably has an inner diameter in the range of 100 micrometer to 2000 micrometer.

In another preferred configuration, the membrane module is a plate-and-frame membrane module.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may also be seen on other views.

FIGS. 1a–1c illustrate one preferred embodiment of the present invention. It should be noted, however, that the present invention may be manifested in a variety of embodiments, and the examples described herein are merely illustrative and are not intended to be limiting. For example, virtually any microfiltration (MF) or ultrafiltration (UF) device wherein a portion of the feed side thereof is coated with a polymeric coating, such as may be in the hollow fiber form, or in a plate-and-frame, or spiral-wound, or other configuration can be utilized in accordance with the present invention.

Referring again to FIGS. 1a–1c, the shell-side of a hollow fiber device may be packed with adsorbent beads commonly used in biomolecule adsorption or chromatography in order to recover and fractionate any mixture of biomolecules/proteins from a lysate or a whole cell broth in one device. The cell lysate or broth or whole cell suspension can be passed through the tube-side of the device as in tangential flow filtration. The solution will permeate through the membrane pores not coated with the polymeric coating and appear on the shell side of the membrane device so as to contact the adsorbent beads. The protein or the biomolecule of interest will be adsorbed on the surfaces and pores of the beads from the permeated solution as it flows through the packed shell side and leaves through the shell-side exit. Typically, two shell-side exit ports are provided in a hollow fiber-based shell-and-tube device. In the embodiment of the present invention shown in FIG. 1a, the shell-side exit on the furthest side from the tube-side inlet can be used for permeate exit. The other exit outlet should, preferably, remain closed during this operation.

This mode of operation of microfiltration-cum-chromatographic adsorption may be preferably carried out for a period long enough to substantially utilize the packed adsorbent bed capacity without achieving a breakthrough of the biomolecule through the permeate exit. In order to prevent breakthrough, the concentration of biomolecule at the permeate exit can be, for example, monitored by an on-line detector (e.g. a UV detector) or predicted by a mathematical model. Then the operation of membrane microfiltration is to be stopped. The elution of the adsorbed biomolecule may be initiated next by opening the permeate side exit port which is kept closed during the microfiltration-cum-adsorption process. As illustrated in FIG. 1b, an eluent may then be passed through the shell-side of the packed bed, and the eluent containing the desorbed biomolecule can exit by the shell-side exit port used in the adsorption part of the cycle for permeate exit.

As shown in FIG. 1b, during this operation of elution of the adsorbed biomolecule from the adsorbent beads packed on the shell-side of the hollow fiber device, the two tube-side outlets, i.e., the inlet and the exit of the hollow fibers, should preferably remain closed.

FIG. 1c illustrates an alternate operational mode for elution which involves introducing the eluent through the hollow fiber inlet employed for broth introduction as seen in FIG. 1a and taking the eluent out through the permeate outlet employed during microfiltration-cum-chromatographic adsorption. However, the broth outlet end of the hollow fiber used during microfiltration-cum-adsorption will remain closed.

The use of a membrane means wherein a portion of the membrane means is coated with a thin layer of polymeric coating in one hollow fiber device as provided by the present invention yields some unexpected advantages when compared with a hollow fiber device containing an uncoated membrane means. The polymeric coating eliminates permeation of proteins through the coated section of the fibers and preferably essentially eliminates water permeation at transmembrane pressure drops used in UF/MF. As a result, the intrinsically high protein adsorption capacity of the selected chromatographic resin beads on the shell side of the membrane device can be fully utilized without any limitation of protein breakthrough through the shell-side permeate outlet. Because of this, protein loading time, feed protein concentration and overall protein loading can be increased considerably using the same amount of resin beads. Further, since the bottom section of the resin bed behaves as if it were a chromatographic column, the chromatographic mechanism can be more fully utilized. One could also have a more uniform transmembrane pressure difference over the length of the membrane which is not coated. FIG. 2a illustrates the concept of the partially coated hollow fiber filtration-cum-chromatography in accordance with the present invention.

In a hollow fiber device, the shell side may be packed with beads by a simple filtration process. The tube-side inlet and outlet are to be closed. Then a slurry of the beads is to be pumped into the shell side from one of the shell-side outlets; the other shell-side outlet should have a screen to hold the beads in place as water goes out through the screen. A similar procedure may be followed for flat membrane devices. Such procedures may be implemented in a laboratory scale or production scale without great difficulty.

Either packing of the beads before or after into the side shell column, the hollow fiber membrane can be partially coated by interfacial polymerization. FIG. 2b illustrates the concept of partial coating of hollow fiber membranes by interfacial polymerization and a coating device.

Hollow fiber or flat membrane modules can be cleaned-in-place (CIP) or sanitized by an appropriate sequence of cleaning solutions (see, for example, van Reis et al. (1991)). The adsorbent particles may be similarly subjected to a CIP procedure (see, for example, Chang and Chase (1996)). One has to ensure that these two procedures are reasonably compatible. To avoid unwarranted introduction of a cleaning solution from one side (e.g., tube side) to the other side (e.g., shell side) in case of some incompatibility, the inlet as well as the exit on the other side should be kept closed, if needed.

The vast majority of conventional hollow fiber membrane-based ultrafiltration and microfiltration devices could be utilized in the present invention. Associated fiber dimensions may vary from 100 $\mu$m I.D. upwards to 2000 $\mu$m I.D. or even higher. The adsorbent beads that are usable with this invention may be 5 $\mu$m and upwards. The adsorbent beads can have any functionality and can have any structure as long as they can stand the small pressure drop (2–10 psi) on the shell side.

Thus, the present invention can achieve protein/biomolecule recovery from a broth through a microfiltration membrane wherein a portion of the feed side thereof is coated with a polymeric coating and its subsequent separation/purification by adsorption on beads on the permeate side of the microfiltration membrane. Furthermore, a mixture of two or three proteins or other biomolecules in a feed can be fractionated by employing an ultrafiltration membrane wherein a portion of the feed side thereof is coated with a polymeric coating in the configuration of FIGS. 1a–1c. The UF membrane will hold larger biomolecules back and allow smaller biomolecules to go through. These permeated biomolecules may then be adsorbed and separated by chromatographic process by the adsorbents on the permeate side of the device. The present invention may also be used with a cellular broth or lystate.

FIG. 1a illustrates the process of loading of the feed solution on the adsorbent bed of the present invention. This loading process differs from loading in both axial flow (conventional) chromatography/adsorption columns and radial flow chromatography columns.

In an axial flow column, the feed is directly loaded on the top part of the adsorbent bed. In a radial flow column, the feed is loaded on the side part of the adsorbent bed via a flow perpendicular to the length of the porous support of the adsorbent bed. In the present invention, the feed is also loaded on the side part of the absorbent bed, but via a tangential flow at the tube side of the hollow fibers as well as by axial flow on the permeate side. Thus, biomolecules permeate through the membrane wherein a portion theeof is coated with a polymeric coating (and is therefore impermeable to proteins) due to transmembrane pressure and diffusion, and the permeated stream appears radially into the packed bed but immediately flows down the column. It should be noted that the present invention can be operated (including loading, filtration and elution) in different positions such as vertical, horizontal or at some angle, although the vertical orientation is the preferred operating position.

As illustrated in FIG. 1b and 1c, the elution of biomolecule adsorbed in the adsorbent bed can be carried out through either the shell side or the tube side of the hollow fiber module, respectively. The elution through the shell side is similar to that in an axial flow column. In the case of elution through the tube side, the eluent flows in the radial direction first, then the eluent flow takes place in the axial direction.

EXPERIMENTAL RESULTS

To demonstrate the utility of the invented process concept and apparatus, experiments were carried out in a hollow fiber membrane module (HFM) to separate the component proteins from binary protein mixtures. The preferred embodiment of the present invention combined the processes of filtration and chromatography into one device or into one hybrid process. A commercially available polysulfone hollow fiber ultrafiltration cartridge was selected based on its molecular weight cut off (MWCO) and the pore size compared with the size of the targeted products to be separated from the broth. Appropriate adsorbent beads were carefully packed in the shell side of the hollow fiber cartridge. A portion of the feed side of the membrane means contained in the hollow fiber cartridge was coated with a thin layer of polyamide coating. The feed solution flowed through the fiber lumina. Particles or compounds in the broth and/or the protein mixtures in solution larger than the membrane pores were rejected and concentrated during filtration, while the smaller components went through the pores which were not coated with the polymeric coating under appropriate transmembrane pressure and were then partitioned onto the adsorbent under proper conditions. Washing and elution was then conducted thereafter in particular ways to fractionate the biomolecules from the shell side.

Ion exchange chromatography was used to demonstrate this technique because it is widely used in the separation of proteins; the relatively mild binding and elution conditions allow high protein recovery with intact biological activity. It plays a critical role in the purification of many proteins, antibodies, nucleic acids, and to a lesser extent peptides. See The Busy Researcher's Guide to Biomolecule Chromatography, 135, PerSeptive Biosystems, Inc. (1996). Bovine serum albumin (BSA, MW 66430), myoglobin (Mb, MW 17566) and alpha-lactalbumin ($\alpha$-LA, MW 14175) were purchased from Sigma (St. Louis, Mo.) and were selected for model protein mixtures due to their differences in pI values. See: Dickerson, R. E., The Structure and Action of Proteins, 52, Harper and Row Publisher (1969); Hirayama, K., Akashi, S., Furuya, M. and Fukuhara, K., Biochemical and Biophysical Research Communications, 173, 639 (1990); Biochemica et Biophysica Acta, 393, 201 (1975); and Townend, R., Weinberger, L. and Timasheff, S. N., J. Amer. Chem. Soc., 82, 3157 (1960). The pI values for BSA, MG and $\alpha$-LA are respectively 4.7, 7.3 and 4.2–4.5. See: Lehniger, A. L., Biochemistry, 162 (1975); Longsworth, L. G. and Jacobsen, C. F., J. Phys. Colloid Chem., 53, 126 (1949); Radola, B. J., Biochemica et Biophysica Acta, 295, 412 (1973); and Kaplan, L. J. and Foster, J. F., Biochemistry, 10, 630 (1971). DEAES-epharose Fast Flow beads were from Pharmacia Biotech (Piscataway, NJ). The beads have an average particle size of 90 $\mu$m. All other chemicals and materials were obtained commercially and were of the highest available quality. The starting buffer was 20 mM Tris-HCl, pH 8.5. All protein solutions were prepared using the starting buffer. Elution buffers were prepared by adding different amounts of NaCl into the starting buffer.

The hollow fiber module used was an UFP-100-E-4A ultrafiltration module (MWCO 100,000) from A/G Technology Corp. (Needham, Mass.). The 36.2 cm long by 1.524 cm I.D. module contained 50 polysulfone fibers. The hollow fibers were 1.6 mm in O.D. and 1.0 mm in I.D. with an effective length of 24.5 cm. The total shell side volume of the module was 20 ml.

Before packing the DEAE-Sepharose beads into the module, the module was thoroughly cleaned and washed with the starting buffer. The ethanol solution in the bead storage container was decanted and replaced with the starting buffer. The beads were washed with the starting buffer three times and equilibrated with the starting buffer. The dilute bead slurry was degassed for 5 minutes in an ultrasonic bath. With both of the tube-side ports closed and the shell-side outlet port covered with a 21 micron polyester mesh, the starting buffer was pumped through the shell-side inlet port using a peristaltic pump. Then the feed was switched to the dilute bead slurry. The beads were densely packed in the shell side of the module from the bottom to the top while the buffer flowed out. After the entire shell-side space was full of beads, the feed was switched back to the starting buffer to flush the packing for 10 more minutes.

Following packing of the DEAE-Sepharose beads into the hollow fiber membrane cartridge, interfacial polymerization was employed to deposit a polyamide coating on the internal diameter of the hollow fibers near the permeate exit. The following two solutions, an aqueous phase and an organic phase, were first prepared for interfacial polymerization:

Organic phase: 1% Sebacoyl chloride ($C_{10}H_{16}Cl_2O_2$, MW 239.14; Sigma, St. Louis, Mo.) in octane (EM Sciences, Cherry Hill, N.J.). Aqueous phase: 1% 1,6-Hexanediamine ($C_6H_{16}N_2$, MW 116.2; Acros, Geel, Belgium) in deionized water (a small amount of an alkaline agent may be used to adjust the pH to 8–10).

The following procedure was developed for coating the internal diameter (I.D.) of part of the length of the fibers.

Before the interfacial polymerization was performed, the module was thoroughly flushed with deionized water for 3 hours to remove the Tris-HCl buffer. A schematic of the coating device is shown in FIG. 2b. With both shell side ports closed so that the shell side was filled with water during the coating operation, the interfacial polymerization was performed as follows:

(1) The 1,6-hexanediamine containing aqueous solution was injected from the bottom tube-side port to fill the fiber lumen fully above the height of the desired coating level with a syringe and was held there for 5 min.

(2) The aqueous solution was drained. The remaining aqueous solution in the tube was blown out using compressed air.

(3) The organic phase was introduced from the bottom of the module (into the fiber lumen) with a feed side adjustable U shape tube to control the organic phase level at 5 cm above the effective bottom of the hollow fibers. After 1 minute, the organic phase was drained. The remaining solution in the hollow fiber lumen was then blown out with compressed air.

(4) With the tube side outlet fully open, the module tube side was rinsed slowly with deionized water at a flow rate of 7.5 ml/min for 30 min at room temperature.

(5) The tube side was further flushed with warm water @ 60° C. for 30 min and then with 0.5 N NaOH solution @ 60° C. for 30 min at a flow rate of about 20 ml/min (this heat treatment allowed the interfacial polymerization reaction to go to completion so that the mechanical strength and solvent resistance of the coating was improved).

(6) The module was cooled down and then flushed first with deionized water and then with 20 mM Tris-buffer, pH 8.5 at room temperature.

The coating length in this instance was about 6 cm, which is about ¼ of the total effective fiber length of 24.5 cm. The procedure can be used for any hydrophilic porous hollow fibers usable for UF/MF. It is not necessary to fill the shell side with beads before the polymeric coating is developed. One can easily introduce the beads after the coating is applied on the fiber I.D.

The experimental setup used in the cleaning, loading and washing steps is shown in FIG. 3. The liquid in the feed reservoir was pumped to the module tube side inlet by a Masterflex 7518-60 peristaltic pump (Cole Parmer, Chicago, Ill.) at the desired flow rate. The operating pressure was controlled by the valve at the tube-side outlet. Both the retentate and the permeate can be recycled if necessary. Before the experiment, the cartridge was cleaned by recycling the 0.5 M NaOH and 0.5 M NaCl cleaning solution at 50° C., then rinsed with deionized water at 50° C. and equilibrated with the starting buffer at room temperature. When loading, the protein solution was fed at a flow rate of 200 ml/min. The operating pressure was 5 psig (34.5 KPag). The retentate was recycled. The permeate was collected and measured for total volume. Both the permeate and the retentate were sampled and assayed for their protein concentrations. After loading, the protein solution remaining in the fiber lumen was drained and the lumen was washed with 50 ml starting buffer while both of the shell side ports were closed.

After loading and washing, tube-side elution was performed on a GradiFrac System from Amersham Pharmacia Biotech (Piscataway, N.J.). The system consisted of a gradient solvent delivery system, a LKB UV monitor at 280 nm wavelength, a conductivity monitor, a REC 102 recorder and a GradiFrac fraction collector. Solvent A (starting buffer) and solvent B (0.5 M NaCl in the starting buffer) were pumped by a LKB1 pump and completely mixed in a mixer forming the elution buffer. The percentage of the solvent B, hence the ionic strength of the elution buffer, was adjusted by the opening of a PSV-50 control valve at the pump outlet. The elution buffer flowed into the tube-side inlet of the module while the tube-side outlet was closed. The eluate came out through the shell-side outlet. Fractions were collected every 2.5 minutes using the GradiFrac fraction collector and assayed for protein concentration using the UV spectrophotometer. Stepwise elution was used for all experiments. Initially, an elution buffer with lower ionic strength was used to elute the weaker charged proteins, then the ionic strength of the elution buffer was increased by increasing the percentage of solvent B to elute the other more highly charged protein. The eluent flow rate was 2.5 ml/min for all elution experiments.

The concentrations of Mb and α-LA in the mixture were determined by the dual-wavelength method using a Hitachi U-2000 (Danbury; Conn.) UV-Vis spectrophotometer at 410 nm and 280 nm.

The partially coated module was tested for water permeation at 5 psig. The water permeation rate declined about 25% when compared to the original module, which agrees very well with the permeable fiber length decrease after coating. The water permeation result indicates that the coating layer is essentially impermeable to water. Detailed results of this analysis are shown in Table 1.

TABLE 1

Water permeation results from hollow fiber membrane module* before coating and after coating.

|  | Before Coating | After Coating | Percentage Reduction |
|---|---|---|---|
| Permeable fiber length (cm) | 24.5 | 18.5 | 24.5% |
| Water Flux at 5 psig (cc/min) | 7.2 | 5.2 | 27.8% |

*Module No: UFP 100-E-4A (A/G Technology, Needham, MA)

The coating layer is chemically and mechanically stable under the common loading, elution, cleaning and sterilization operations. Especially during the cleaning operation, the coating layer can endure the hot, caustic cleaning solution and high shear stress. The coated module still functioned well after more than a year of experiments.

The coating blocks the membrane pores near the module outlet zone, making the bottom length of the hollow fiber, in this case the bottom ¼, essentially impermeable to liquid and protein at the pressure drop applied in UF/MF since the coating conditions create a membrane suitable for reverse osmosis which requires much higher ΔP for water permeation. This in effect increases the bed utilization factor without increasing the permeate outlet back pressure by moving the point of maximum permeate flow away from the permeate outlet. As a result, during the protein loading step, there is almost no permeate emerging onto the shell side from the tube side near the shell-side permeate outlet. Therefore, early protein leakage due to protein introduction into the shell side near the shell-side permeate outlet from the tube-side feed solution is eliminated. Consequently, the protein leakage into the permeate solution observed in the uncoated module is drastically reduced. Correspondingly, the overall protein loading capacity of the shell-side bed is substantially increased in the coated module.

This change introduces a new membrane filtration-cum-chromatography device: a hollow fiber device which for most of its length functions as it should in conventional UF/MF while the rest of the fiber length is essentially shut off from a filtration point of view. Correspondingly, the beads on the shell side for this latter section of the device can act as a conventional resin bed which has considerable adsorption/fractionation capacity whereas the rest of the resin bed on the shell side performs as in the uncoated module. This configuration results in considerable benefits, specifically, in achieving a longer protein-loading time without significant protein leakage from the shell-side permeate outlet. Further, the protein adsorption capacity is considerably increased.

FIG. 4 shows the breakthrough behavior of two identical UF modules (UFP-100-4A) for the protein myoglobin (Mb). Both modules have essentially identical amounts of resin beads on the shell side of the module. However, one module has a coating (length of coating, 6 cm) of the interfacially-polymerized coating type on the I.D. of the fibers 24.5 cm long. It was observed that the module having the coating has a much larger adsorption capacity than the uncoated module. If the breakthrough time in the module having uncoated membrane is assumed to be, say, 10 minutes, that in the coated module is 50 minutes, signifying 5 times higher capacity. The operational conditions are identical, however, for both modules. Table 2 illustrates the Mb breakthrough results for both the uncoated module and the module having fibers part of whose length was coated with an essentially impermeable layer (FIG. 4).

TABLE 2

Comparison of the breakthrough times for Mb between the modules before coating and after coating.

|  | Uncoated module | Partially coated fiber module |
|---|---|---|
| Feed Mb Conc. (μg/ml) | 250 | 250 |
| Breakthrough time* (min) | 10 | 50 |

*The breakthrough time is defined as the point when protein concentration in the permeate flow reaches 10% of the protein concentration in the feed.

In FIGS. 5a and 5b, it can be seen that the performance of the partially coated module (FIG. 5b) is very close to that of the uncoated module (FIG. 5a) for the elution-separation of Mb and α-LA. Note that the tube-side loading in each case was for 15 minutes and the peak profiles for the two proteins are essentially identical for the partially coated module and the uncoated module. These conditions, however, are such that the uncoated module was close to having breakthrough of the proteins.

On the other hand, FIGS. 6a and 6b show the elution profiles of the same two proteins (Mb and α-LA) from the module having partially coated fibers for two different conditions: the first one (FIG. 6a) where the loading was carried out for 55 minutes under feed conditions similar to that of FIG. 5; the second one (FIG.-6b) where the loading was carried out for 25 minutes under the same feed flow rate as in FIG. 5 but the feed protein concentrations were 5–6 times larger than those in FIG. 5. As a result, both conditions in FIG. 6 show much higher protein concentrations in the eluate. In fact, the total protein recovered in FIG. 6b is about 7 times for Mb as well as for α-LA compared to those in FIG. 5a. Yet there was no breakthrough of the proteins from the partially coated fiber-based columns in spite of the high amount of protein loading.

The effect of partial coating on the protein leakage reduction and protein loading capacity increase shown in the above experiments is summarized in Table 3.

TABLE 3

Comparison of the experimental conditions and protein loading results for the module before coating and after coating.

| | Before coating | After partial coating | | |
|---|---|---|---|---|
| | FIG. 5a | FIG. 5b | FIG. 6a | FIG. 6b |
| Feed conc. (μg/ml) | 50 | 50 | 50 | 260 |
| Feed flow rate (ml/min) | 200 | 200 | 200 | 200 |
| Feed pressure (psig) | 5 | 5 | 5 | 5 |
| Loading time (min) | 15 | 15 | 55 | 25 |
| Permeate flow rate (ml/min) | 5.9 | 5.3 | 5 | 4.52 |
| Ave. Mb conc. in permeate (μg/ml) | 0.97 | 0.56 | 1.1 | 0.97 |
| Total Mb loaded (mg) | 3.2 | 3.08 | 9.56 | 23 |

The effect of the coating on separation results for another pair of proteins, namely Mb and BSA, is similar to that of Mb/α-LA. FIG. 7a illustrates the protein separation profiles obtained from the uncoated module. On the other hand, FIG. 7b shows the significantly increased loading capacity after the membrane pores near the outlet area were rendered essentially impermeable by interfacial polymerization-based coating. The loading amount of BSA is smaller than that of α-LA due to its larger molecular size.

The effect of coating on the performance of a hollow fiber microfiltration membrane (CFP-1-E4A, pore size 0.1 μm, Amersham Biosciences) module can be seen with reference to FIGS. 8 and 9. DEAE Sepharose Fast Flow beads were packed in the shell side of the hollow fiber MF module. A similar coating procedure was applied to coat the bottom section (about ¼ of the total length) of the hollow fiber microfiltration membranes. As shown in FIGS. 8 and 9, the protein separation capacities were greatly increased after the bottom section of the hollow fiber microfiltration membrane was coated with an interfacially polymerized film. Furthermore, in such a device comprised of a coated microfiltration membrane, much more BSA and α-LA can be loaded compared to a device using an ultrafiltration membrane, because of their molecular size and shape. The results show that the membrane and adsorbent can be tailored to improve the protein selectivity.

Four loading-elution-regeneration-based cyclic runs for Mb and α-LA were performed with a synthetic yeast fermentation broth feed without cleaning in between runs. The Mb and α-LA elution profiles for different runs, as shown in FIG. 10, are almost superimposable. Due to the much lower transmembrane flux in this device plus the periodic elution and regeneration, the device did not suffer from the problem of "fouling" that is apt to occur in conventional microfiltration.

Other manifestations and geometrical configurations according to the present invention could be designed easily and used for biomolecule separation. The present invention can be easily applied to the direct separation of proteins from a cellular broth.

Thus, a hollow fiber ultrafiltration cartridge was successfully packed on the shell side with DEAE Sepharose Fast Flow anion exchange beads for separation of biomolecules via an integrated filtration-cum-chromatography process, interfacial polymerization was used to coat a portion of the internal diameter of the hollow fiber membrane with a polyamide coating near the permeate exit and mixtures of Mb and α-LA were efficiently separated in the shell-side bed which acted as an ion exchange chromatographic column. Mixtures of Mb and BSA were also separated through the integrated filtration-cum-chromatography process of the present invention.

The present invention may also be used with, for example, a feed solution of two or three proteins in an unclarified broth or a homogenate flowing through the tube side in a straightforward manner.

The present invention could also comprise hollow fibers or flat membranes having functional groups attached to the pore surfaces; in such a case, the pore surfaces could provide additional adsorption capacity or selectivity beyond that available in the bed of adsorbents incorporated in the permeate side of the ultrafiltration/microfiltration module.

Furthermore, the present invention is also applicable to centrifugally driven ultrafiltration/microfiltration processes. By way of example, the present invention can be used to isolate, recover and partially purify proteins and other factors from the milk of transgenic animals; in particular, ultrafiltration membranes would be employed in such applications.

Additionally, pores in microfiltration membranes may have grafted affinity ligands, e.g., protein A/G to adsorb appropriate proteins/antibodies from the permeate flowing through the pores.

References cited herein are hereby incorporated by reference in their entirety.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

What is claimed is:

1. A membrane module means for recovering bioproducts from a feed solution, said means comprising a module housing, having a permeate outlet means, membrane means disposed in said housing for filtering the bioproducts from the feed solution wherein a portion of the feed side of the membrane means, positioned close to the permeate outlet means, is coated with a polymeric coating so as to render such portion impermeable to the bioproducts to be recovered, and an adsorbent bed means disposed in said housing for retaining the bioproducts which permeate through the membrane means, wherein the membrane module means is adapted to allow fractionation and purification of the retained byproducts from the bed by elution.

2. The membrane module means according to claim 1 wherein the polymeric coating is selected from the group consisting of polyamides, polysulfones, polyethersulfones, aromatic polyamides, polyvinylalcohols, polyacrylonitriles, polyethyleneimines, polyureas, polyvinylidene fluorides and polydimethylsiloxanes.

3. The membrane module means according to claim 1 wherein the membrane means is coated with the polymeric coating by interfacial polymerization.

4. The membrane module means according to claim 1 wherein the polymeric coating covers about one-sixteenth to about one-half of the membrane means.

5. The membrane module means according to claim 4 wherein the polymeric coating covers about one-quarter of the membrane means.

6. The membrane module means according to claim 1 wherein the polymeric coating is essentially impermeable to water.

7. A system comprising a plurality of membrane module means according to claim 1.

8. The system according to claim 7 wherein at least two of the modules are connected in parallel.

9. An apparatus for recovering bioproducts from a feed solution, said apparatus comprising:
 a housing having a feed inlet means, a feed outlet means, and a permeate outlet means;
 at least one membrane means disposed within the housing and having a feed side and a permeate side wherein a portion of the feed side of the membrane means, positioned close to the permeate outlet means, is coated with a polymeric coating so as to render such portion impermeable to the bioproducts to be recovered; and
 a packed bed of adsorbent particles disposed within the housing in contact with the permeate side of the membrane;
 wherein the feed inlet means allows the feed solution to pass into contact with the permeate side of the membrane;
 wherein bioproducts are separated from the feed solution by permeation to the permeate side of the membrane means;
 wherein the permeated bioproducts contact the packed bed;
 wherein the bioproducts are retained by the adsorbent particles; and
 whereby the bioproducts are isolated from the feed solution.

10. The apparatus according to claim 9 wherein the polymeric coating is selected from the group consisting of polyamides, polysulfones, polyethersulfones, aromatic polyamides, polyvinylalcohols, polyacrylonitriles, polyethyleneimines, polyureas, polyvinylidene fluorides and polydimethylsiloxanes.

11. The apparatus according to claim 9 wherein the membrane means is coated with the polymeric coating by interfacial polymerization.

12. The apparatus according to claim 9 wherein the polymeric coating covers about one-sixteenth to about one-half of the membrane means.

13. The apparatus according to claim 12 wherein the polymeric coating covers about one-quarter of the membrane means.

14. The apparatus according to claim 9 wherein the polymeric coating is essentially impermeable to water.

15. The apparatus according to claim 9 wherein the polymeric coating is positioned at the bottom of the membrane means.

16. The apparatus according to claim 9 further comprising means to control the inlet flow of the feed solution.

17. The apparatus according to claim 9 wherein the bioproducts retained by the adsorbent particles are capable of being eluted directly from said apparatus.

18. The apparatus according to claim 9 wherein the housing is adapted to allow introduction of an elution solution, wherein the bioproducts are capable of being purified in situ by passing the elution solution over the adsorbent particles disposed in the membrane module.

19. The apparatus according to claim 9 wherein said apparatus is adapted to allow an elution solution to pass through the membrane and into contact with the adsorbent particles in order to purify the retained bioproducts.

20. The apparatus according to claim 9 wherein the adsorbent particles are chromatographic matrix particles.

21. The apparatus according to claim 9 wherein the adsorbent particles are adsorbent beads.

22. The apparatus according to claim 9 wherein the adsorbent particles further comprise affinity ligands attached thereto.

23. The apparatus according to claim 9 wherein the adsorbent particles reduce the differences in transmembrane pressure along the length of the feed solution flow path between the feed inlet means and the feed outlet means.

24. The apparatus according to claim 9 wherein the membrane means is a microfiltration membrane.

25. The apparatus according to claim 9 wherein the membrane means is an ultrafiltration membrane.

26. The apparatus according to claim 9 wherein the apparatus is a hollow fiber membrane module having at least one hollow fiber.

27. The apparatus according to claim 26 wherein the at least one hollow fiber comprises a plurality of hollow fibers.

28. The apparatus according to claim 26 wherein the adsorbent particles are disposed on the shell side of the hollow fiber, and wherein the feed solution is passed through the tube side of the hollow fiber.

29. The apparatus according to claim 26 wherein the module is provided with a permeate-side inlet means and a permeate-side outlet means.

30. The apparatus according to claim 26 wherein the hollow fiber has an inner diameter in the range of 100 micrometer to 2000 micrometer.

31. The apparatus according to claim 9 wherein the membrane module is a plate-and-frame membrane module.

32. A method of recovering bioproducts from a feed solution, the method comprising:
 providing a membrane module comprising a housing, at least one membrane means disposed within the housing and having a feed side, a permeate side, and a permeate outlet means, and wherein a portion of the feed side of the membrane means, positioned close to the permeate outlet means, is coated with a polymeric coating so as to render such portion impermeable to the bioproducts to be recovered, and a packed bed of adsorbent particles disposed within the housing in contact with the permeate side of the membrane means;
 passing the feed solution into the membrane module to contact the feed side of the membrane; and
 separating bioproducts from the feed solution by permeation through to the permeate side of the membrane means and allowing the permeated bioproducts to contact the adsorbent particles, wherein the bioproducts are retained by the adsorbent particles, whereby the bioproducts are isolated from the feed solution.

33. The method according to claim 32 wherein the polymeric coating is selected from the group consisting of polyamides, polysulfones, polyethersulfones, aromatic polyamides, polyvinylalcohols, polyacrylonitriles, polyethyleneimines, polyureas, polyvinylidene fluorides and polydimethylsiloxanes.

34. The method according to claim 32 wherein the membrane means is coated with the polymeric coating by interfacial polymerization.

35. The method according to claim 32 wherein the polymeric coating covers about one-sixteenth to about one-half of the membrane means.

36. The method according to claim 35 wherein the polymeric coating covers about one-quarter of the membrane means.

37. The method according to claim 32 wherein the polymeric coating is essentially impermeable to water.

38. The method according to claim 32 wherein the polymeric coating is positioned at the bottom of the membrane means.

39. The method according to claim 32 further comprising terminating the introduction of feed solution into the membrane module before the packed bed becomes saturated.

40. The method according to claim 32 further comprising terminating the introduction of feed solution into the membrane module before breakthrough of the bioproducts occurs at the feed outlet of the membrane module.

41. The method according to claim 32 further comprising eluting the bioproducts retained by the adsorbent particles disposed in the membrane module.

42. The method according to claim 32 further comprising purifying the bioproducts by passing an elution solution over the adsorbent particles disposed in the membrane module.

43. The method according to claim 32 further comprising passing an elution solution through the membrane means and into contact with the adsorbent particles in order to purify the retained bioproducts.

44. The method according to claim 32 wherein the adsorbent particles are chromatographic matrix particles.

45. The method according to claim 32 wherein the adsorbent particles are adsorbent beads.

46. The method according to claim 32 wherein the adsorbent particles further comprise affinity ligands attached thereto.

47. The method according to claim 32 wherein the adsorbent particles reduce the differences in transmembrane pressure along the length of the feed solution flow path through the module.

48. The method according to claim 32 wherein the membrane means is a microfiltration membrane.

49. The method according to claim 32 wherein the membrane means is an ultrafiltration membrane.

50. The method according to claim 32 wherein the membrane module is a hollow fiber membrane module having at least one hollow fiber.

51. The method according to claim 50 wherein the adsorbent particles are disposed on the shell side of the hollow fiber, and wherein the feed solution is passed through the tube side of the hollow fiber.

* * * * *